United States Patent [19]

Oude Alink

[11] 4,113,730

[45] Sep. 12, 1978

[54] PREPARATION OF OCTAHYDROPHENANTHRIDINES

[75] Inventor: Bernardus A. Oude Alink, St. Louis, Mo.

[73] Assignee: Petrolite Corporation, St. Louis, Mo.

[21] Appl. No.: 812,888

[22] Filed: Jul. 5, 1977

[51] Int. Cl.$^2$ .......................................... C07D 217/02
[52] U.S. Cl. ............................... 260/286 A; 252/390; 44/72; 544/231
[58] Field of Search .................................... 260/286 A

[56] References Cited

U.S. PATENT DOCUMENTS

| 3,816,428 | 6/1974 | Redmore | 260/279 R |
| 3,931,191 | 1/1976 | Alink | 260/290 P |

*Primary Examiner*—Donald G. Daus
*Assistant Examiner*—Lisa Jones
*Attorney, Agent, or Firm*—Sidney B. Ring; Hyman F. Glass

[57] ABSTRACT

This invention relates to the preparation of octahydrophenanthridines by the deammoniation of tetrahydropyrimidines; and to the products thereof.

5 Claims, No Drawings

PREPARATION OF OCTAHYDROPHENANTHRIDINES

In Ser. No. 292,494, now U.S. Pat. No. 4,085,104, Apr. 18, 1978 filed on Sept. 27, 1972 there is described and claimed substituted 2,3,4,5-tetrahydropyrimidines (THP)

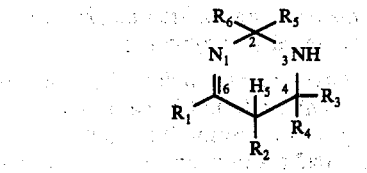

which are prepared by the following reactions:

1. The reaction of a carbonyl compound (ketone or aldehyde) with ($NH_3$ or $NH_4OH$) and a sulfur-containing catalyst.
2. The reaction of an $\alpha,\beta$-unsaturated ketone and a carbonyl compound and $NH_3$ (or $NH_4OH$) without a catalyst.
3. Reaction of an $\alpha,\beta$-unsaturated ketone, a 1-aminoalcohol and $NH_3$ (or $NH_4OH$) without a catalyst.

In the above formula, $R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escoscyl, docosyl, etc. for example having about 1-25 or more carbons such as from about 1-18 carbons, but preferably about 1-12 carbons. The term "alkyl" also includes isomers of the straight chain where branching occurs.

Cycloalkyl includes cyclopentyl, cyclohexyl, etc. and derivatives thereof such as alkyl cyclohexyl, dialkylcyclohexyl, etc.

Aryl, alkaryl and aralkyl include phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula

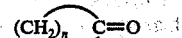

such as cyclohexanone, cyclopentanone, substituted derivatives thereof such as alkyl-cyclohexanone, dialkyl-cyclohexanone.

Ser. No. 384,440 filed Aug. 1, 1973 (U.S. Pat. No. 3,931,191) discloses that the tetrahydropyrimidines of said Ser. No. 292,494 U.S. Pat. No. 4,085,104 can be converted to substituted pyridines according to the following equation:

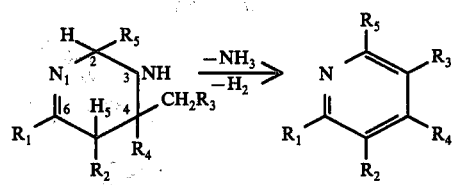

provided the 2-position of THP contains at least 1 hydrogen and one of the groups attached to carbon 4 of THP has at least one methylene group.

The meaning of $R_1$, $R_2$, $R_3$, $R_4$, $R_5$ are the same as stated above.

The reaction is carried out by heating THP at a temperature sufficiently high to remove ammonia and hydrogen so as to cause rearrangement to the pyridine compound. In general, the temperature employed is from about 60°–400° C. or higher, such as from about 75°–350°, but preferably from about 90°–250° C. with an optimum of about 200° to 250° C. Reduced pressure may be employed as desired so as to aid in removal of $NH_3$ and $H_2$.

The reaction can be carried out with or without a catalyst. Where a catalyst is employed it is generally of the Lewis acid type. Typical catalysts include salts, such as of inorganic or organic acids for example ammonium or amine salts of the formula

where Ⓝ is ammonium or amine and X is an anion for example a halide (Cl, Br, F, I), a carboxylic acid, a sulfonic acid, etc. Illustrative examples include

| | |
|---|---|
| $NH_4$ acetate | $NH_4I$ |
| $NH_4Cl$ | $NH_4$ benzenesulfonate, etc. |
| $NH_4Br$ | |

Zinc halides such as zinc chloride, silica, etc. Other catalysts include $AlCl_3$, $FeCl_3$, PbO, $Al_2O_3$, etc.

U.S. Pat. No. 3,931,191 states that pyridines are formed in accordance with its process provided the 2-position of THP contains at least 1 hydrogen.

I have now unexpectedly discovered that tetrahydropyrimidines containing no hydrogens in the 2-position (i.e., disubstituted in the 2-position) can be converted to octahydrophenanthridines upon deammoniation under conditions similar to U.S. Pat. No. 3,931,191.

The deammoniation is carried out in the manner of U.S. Pat. No. 3,931,191, with or without a catalyst.

The reaction of this invention may be summarized as follows:

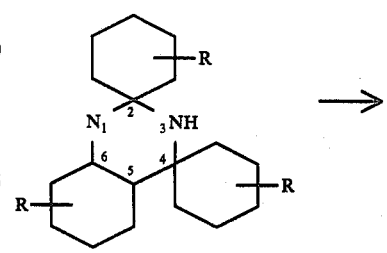

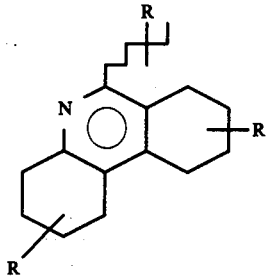

where R is hydrogen or a substituted group, for example alkyl, cycloalkyl, aryl, aralkyl, alkaryl, etc.

These octahydropyrimidines are dehydrogenated to phenanthridines according to the following reaction:

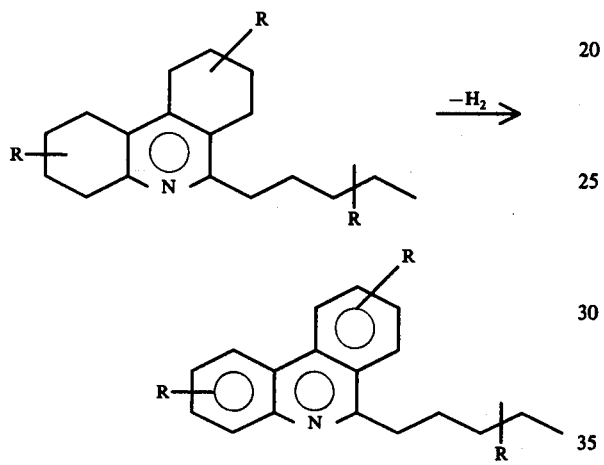

The following examples are presented by way of illustration and not of limitation.

EXAMPLE 1

2,2,4,4-Dipentamethylene 5,6-tetramethylene 2,3,4,5-tetrahydropyrimidine

A mixture of 294 grams of cyclohexanone and 5 grams of ammonium chloride was placed in a pressure reactor. Over a ¾ hour period 38.8 grams of ammonia gas was added. After the addition was complexed, the mixture was stirred for 5 hours at ambient temperature. The product was taken up in toluene and the aqueous phase which separated was discarded. The toluene solution was evaporated under diminished pressure to yield 268 grams of 2,2,4,4-dipentamethylene 5,6-tetramethylene 2,3,4,5-tetrahydropyrimidine, infrared spectrum 6.02 μ (C=N) and 3.05 μ (N—H), $C^{13}$ nuclear magnetic resonance spectrum, solvent $CDCl_3$, ref. TMS:

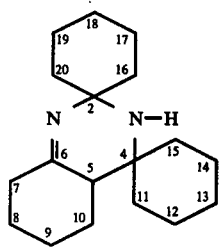

70.11 (2); 50.16 (4); 46.59 (5);
169.38 (6); 42.43 (7); 29.30 (8);
26.38 (9); 29.30 (10); 40.61 (11);
21.90*(12; 26.38 (13); 21.64*(14);
35.54 (15); 38.53 (16); 22.55*(17);
26.38 (18); 22.55*(19); 38.53 (20).

*values may be interchanged.

EXAMPLE 2

9,13,18-Trimethyl 2,2,4,4-dipentamethylene-5,6-tetramethylene 2,3,4,5-tetrahydropyrimidine A mixture of 75 grams of 4-methylcyclohexanone, 6.1 grams of ammonium chloride and 300 grams of toluene were placed in a pressure reactor. To the mixture was added with stirring 16.2 grams of ammonia gas over a 15 minute period. After the addition was completed, the mixture was stirred for 20 hours. The aqueous layer was removed and the toluene layer evaporated under diminished pressure to yield 66 grams of 9,13,18-trimethyl 2,2,4,4-dipentamethylene 5,6-tetramethylene 2,3,4,5-tetrahydropyrimidine, infrared spectrum 6.01 μ (C=N), 3.08 μ (N—H), $C^{13}$ nuclear magnetic resonance spectrum, solvent $CDCl_3$, reference T.M.S., δ in ppm.

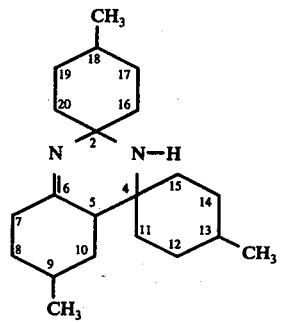

69.93 (2); 49.67 (4); 47.14 (5);
169.60 (6); 39.41 (7); 34.67 (8);
32.37 (9); 34.67 (10); 40.58 (11);
29.80 (12); 32.79 (13); 29.80 (14);
36.95 (15); 37.85 (16); 31.17 (17);
32.79 (18); 31.17 (19); 37.85 (20);
21.95 (9-$CH_3$); 22.40 (13-$CH_3$);
22.40 (18-$CH_3$).

EXAMPLE 3

9-Pentyl 1,2,3,4,5,6,7,8-octahydrophenanthridine

A sample of 117.6 grams of 2,2,4,4-dipentamethylene 5,6-tetramethylene 2,3,4,5-tetrahydropyrimidine, prepared as described in example 1, 2 grams of ammonium chloride, and 73 grams of xylene were refluxed for 18 hours. Ammonium gas evolved during the reaction. The xylene was distilled off and the resulting product distilled under diminished pressure, to yield 65 grams of 9-pentyl 1,2,3,4,5,6,7,8-octahydrophenanthridine; b.$_{0.1}$ 160°-178° C.; infrared spectrum 6.40 μ; ultraviolet spectrum, $\lambda_{max.}^{MeOH}$ 2730 Å; $C^{13}$ nuclear magnetic resonance spectrum; solvent $CDCl_3$, reference T.M.S., δ in ppm:

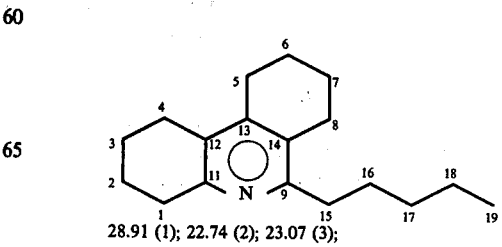

28.91 (1); 22.74 (2); 23.07 (3);

-continued
25.34 (4); 26.18 (5); 22.74 (6);
23.07 (7); 25.92 (8); 156.98 (9);
152.36 (11); 126.83 (12);
143.91 (13); 127.22 (14); 35.09 (15);
32.23 (16); 32.94 (17); 21.70 (18);
14.03 (19).

Anal. Calc.ed for $C_{18}H_{27}N$; N, 5.45; Found N, 5.31.

EXAMPLE 4

9-Pentyl 1,2,3,4,5,6,7,8-octahydrophenanthridine

A sample of 313 grams of 2,2,4,4-dipentamethylene 5,6-tetramethylene 2,3,4,5-tetrahydropyrimidine, prepared as described in example 1, and 1 gram of ammonium chloride was heated for 1 hour at 157° C.; for 1 hour at 194° C. and for 16 hours at 205° C. Ammonia gas was evolved during the reaction. Distillation under diminished pressure yielded 9-pentyl 1,2,3,4,5,6,7,8-octahydrophenanthridine identical in all respects to the product described in example 3.

EXAMPLE 5

9-Pentyl phenanthridine

A mixture of 20 grams of 9-pentyl 1,2,3,4,5,6,7,8-octahydrophenanthridine, prepared as described in example 3, 108 grams of an alkylated benzene solvent and 4 grams of a 5% Palladium/Al catalyst were refluxed for 19 hours. Hydrogen gas was evolved during the reaction. The solvent was removed under diminished pressure to yield after work-up 18 grams of 9-pentyl phenanthridine; infrared spectrum, 6.41; 6.65; and 6.72 μ; $C^{13}$ nuclear magnetic resonance spectrum, solvent $CDCl_3$, ref. T.M.S.; δ in ppm.:

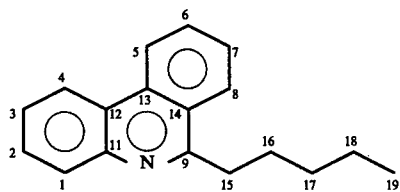

129.60 (1); 125.77 (2); 128.11 (3);
121.61 (4); 122.07 (5); 126.75 (6);
125.77 (7); 129.60 (8); 161.61 (9);
143.69 (11); 123.37 (12);
131.52 (13); 124.93 (14); 35.91 (15);
28.70 (16); 32.08 (17); 22.60 (18);
14.02 (19).

EXAMPLE 6

3,7,17-Trimethyl 9-pentyl 1,2,3,4,5,6,7,8 octahydrophenanthridine

A sample of 50 grams of 9,13,18-trimethyl 2,2,4,4-dipentamethylene 5,6-tetramethylene 2,3,4,5-tetrahydropyrimidine, prepared as described in example 2, and 0.5 grams of ammonium chloride was heated for 19 hours at 203° C. Ammonia gas was evolved during the reaction. There was isolated 45 grams of 3,7,17-trimethyl 9-pentyl 1,2,3,4,5,6,7,8-octahydrophenanthridine, $b_{0.1}$, 170°–188° C., infrared spectrum 6.4 μ; ultraviolet spectrum $\lambda_{max.}^{MeOH}$ 2750 Å, $C^{13}$ nuclear magnetic resonance spectrum, solvent $CDCl_3$, ref. T.M.S. δ in ppm:

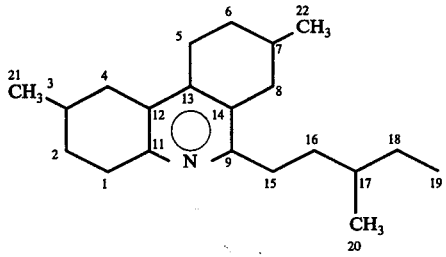

28.76*(1); 31.49**(2);
28.24*(3); 34.93***(4);
26.82 (5); 31.04**(6);
29.28*(7); 33.96***(8);
155.96 (9); 150.70 (11); 127.78 (12);
146.55 (13); 128.04 (14); 32.01**(15);
35.97 (16); 33.96***(17);
30.19(18);  (18); 11.36 (19); 19.09 (20);
21.75 (21); 21.75 (22).

Anal. Calc.ed for $C_{21}H_{33}N$; N, 4.68; Found N, 4.45.

EXAMPLE 7

Mixed trimethyl 9-Pentyl 1,2,3,4,5,6,7,8-octahydrophenanthridine

A mixture of 284 grams of 3-methylcyclohexanone, 19 grams of ammonium chloride and 220 grams of toluene was placed in a pressure reactor. To the mixture was added over a ½ hour period, 60 grams of ammonia gas and the mixture was stirred for 18 hours. The aqueous phase produced was separated and the toluene solution evaporated under diminished pressure.

The remaining product was heated for 19 hours at 210° C. A sample of 150 grams of the resulting product was distilled under diminished pressure and the fraction 106 grams, $b_{0.1}$, 173°–180° C., was identified as a mixture of trimethyl 9-pentyl octahydrophenanthridines; infrared spectrum 6.4; ultraviolet spectrum $\lambda_{max.}^{MeOH}$ 2750 Å; $C^{13}$ nuclear magnetic resonance spectrum, solvent $CDCl_3$, ref. T.M.S., δ in ppm.

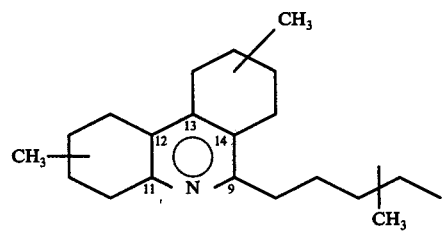

156.81 (9); 155.96 (9);
152.13 (11); 151.94 (11);
143.43 (13); 142.78 (13);
142.46 (13); 126.88 (12 or 14);
126.49 (12 or 14); 126.29 (12 or 14).

Anal. Calc.ed for $C_{21}H_{33}N$; N, 4.68; Found 4.41

The compositions of this invention are useful as corrosion inhibitors, biocides, fuel additives, fuel antifoulants, scale inhibitors, antistatic agents, chelating agents, etc.

It will be apparent that various changes and modifications may be made in the invention described herein without departing from the scope of the invention. It is intended, therefore, that all matter shall be interpreted as illustrative and not as limitative.

I claim:

1. A process of converting 2,3,4,5-tetrahydropyrimidines of the formula

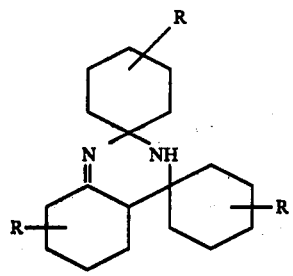

to octahydrophenanthridines of the formula

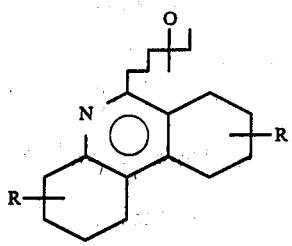

where R is hydrogen or alkyl of from one to 25 carbon atoms, which comprises the step of heating said tetrahydropyrimidines to a temperature between 75° C. and 350° C. sufficiently high to remove ammonia and hydrogen so as to form said octahydrophenanthridines.

2. The process of claim 1 where a Lewis acid catalyst is employed.

3. The process of claim 2 where the Lewis acid catalyst is an ammonium salt.

4. The process of claim 3 where the ammonium salt is an ammonium salt of an inorganic or organic acid.

5. The process of claim 3 where the ammonium salt is ammonium chloride or ammonium acetate.

* * * * *